United States Patent
Norris et al.

(10) Patent No.: US 9,095,466 B2
(45) Date of Patent: Aug. 4, 2015

(54) APPOSITION FIBER FOR USE IN ENDOLUMINAL DEPLOYMENT OF EXPANDABLE DEVICES IN TORTUOUS ANATOMIES

(75) Inventors: Patrick M. Norris, Bellemont, AZ (US); Stephanie M. Walsh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 766 days.

(21) Appl. No.: 13/297,007

(22) Filed: Nov. 15, 2011

(65) Prior Publication Data

US 2012/0296360 A1 Nov. 22, 2012

Related U.S. Application Data

(60) Provisional application No. 61/414,198, filed on Nov. 16, 2010.

(51) Int. Cl.
| | |
|---|---|
| A61F 2/06 | (2013.01) |
| A61F 2/97 | (2013.01) |
| A61F 2/95 | (2013.01) |
| A61F 2/966 | (2013.01) |

(52) U.S. Cl.
CPC ............ *A61F 2/97* (2013.01); *A61F 2002/9511* (2013.01); *A61F 2002/9665* (2013.01)

(58) Field of Classification Search
CPC ................. A61F 2002/9511; A61F 2002/9665; A61F 2/97
USPC ................. 606/108, 200; 623/1.11, 1.12, 1.23
See application file for complete search history.

(56) References Cited

U.S. PATENT DOCUMENTS

| | | | |
|---|---|---|---|
| 5,713,948 A | 2/1998 | Uflacker | |
| 5,776,186 A | 7/1998 | Uflacker | |
| 5,873,906 A * | 2/1999 | Lau et al. | ..................... 623/1.12 |
| 6,086,610 A | 7/2000 | Duerig et al. | |
| 6,106,549 A | 8/2000 | Taheri | |
| 6,602,288 B1 | 8/2003 | Cosgrove et al. | |
| 6,974,471 B2 | 12/2005 | Van Schie et al. | |
| 7,318,835 B2 | 1/2008 | Berra | |
| 7,335,224 B2 | 2/2008 | Ohlenschlaeger | |
| 7,608,114 B2 | 10/2009 | Levine et al. | |
| 7,651,519 B2 | 1/2010 | Dittman | |
| 7,666,219 B2 | 2/2010 | Rasmussen et al. | |

(Continued)

FOREIGN PATENT DOCUMENTS

| | | |
|---|---|---|
| GB | 2464977 | 3/2010 |
| WO | 98/42276 | 10/1998 |

(Continued)

OTHER PUBLICATIONS

Kobel, T et al. In Situ Bending of a Thoracic Stent-Graft: A Proposed Novel Technique to Improve Thoracic Endograft Seal, J Endovasc Ther; 2008; 15:62-66.

*Primary Examiner* — Julian W Woo
(74) *Attorney, Agent, or Firm* — Gilbert R. Gabo

(57) ABSTRACT

A catheter assembly includes an expandable device that is disposed at a distal end of a catheter and expandable toward a fully deployed outer dimension. A fiber extends from the catheter and is releasably coupled to a side wall of the expandable device near or at an end of the expandable device to maintain an inner curvature of the expandable device as the expandable device is deployed.

12 Claims, 10 Drawing Sheets

(56) References Cited

U.S. PATENT DOCUMENTS

| | | |
|---|---|---|
| 7,758,626 B2 | 7/2010 | Kim et al. |
| 7,803,177 B2 | 9/2010 | Hartley et al. |
| 7,854,758 B2 | 12/2010 | Taheri |
| 2003/0088305 A1 | 5/2003 | Van Schie et al. |
| 2003/0208260 A1 | 11/2003 | Lau et al. |
| 2006/0247757 A1 | 11/2006 | Kaufmann et al. |
| 2007/0088424 A1 | 4/2007 | Greenberg et al. |
| 2007/0168013 A1 | 7/2007 | Douglas |
| 2007/0267101 A1 | 11/2007 | Wong |
| 2008/0039925 A1 | 2/2008 | Ishimaru et al. |
| 2008/0114440 A1 | 5/2008 | Hlavka |
| 2008/0264102 A1 | 10/2008 | Berra |
| 2008/0294234 A1 | 11/2008 | Hartley et al. |
| 2009/0099640 A1 | 4/2009 | Weng |
| 2009/0216308 A1 | 8/2009 | Hartley |
| 2009/0259291 A1 | 10/2009 | Kolbel et al. |
| 2009/0264980 A1 | 10/2009 | Mackay |
| 2010/0049293 A1 | 2/2010 | Zukowski et al. |
| 2010/0094401 A1 | 4/2010 | Kolbel et al. |
| 2010/0114291 A1 | 5/2010 | Kolbel et al. |
| 2010/0168838 A1 | 7/2010 | Hartley et al. |

FOREIGN PATENT DOCUMENTS

| | | |
|---|---|---|
| WO | 2008/047092 | 4/2008 |
| WO | 2008/140796 | 11/2008 |
| WO | 2009/091718 | 7/2009 |
| WO | 2009/102441 | 8/2009 |
| WO | 2009/126227 | 10/2009 |
| WO | 2010/042210 | 4/2010 |
| WO | 2010/062355 | 6/2010 |
| WO | 2010/063795 | 6/2010 |
| WO | 2010/105195 | 9/2010 |

\* cited by examiner

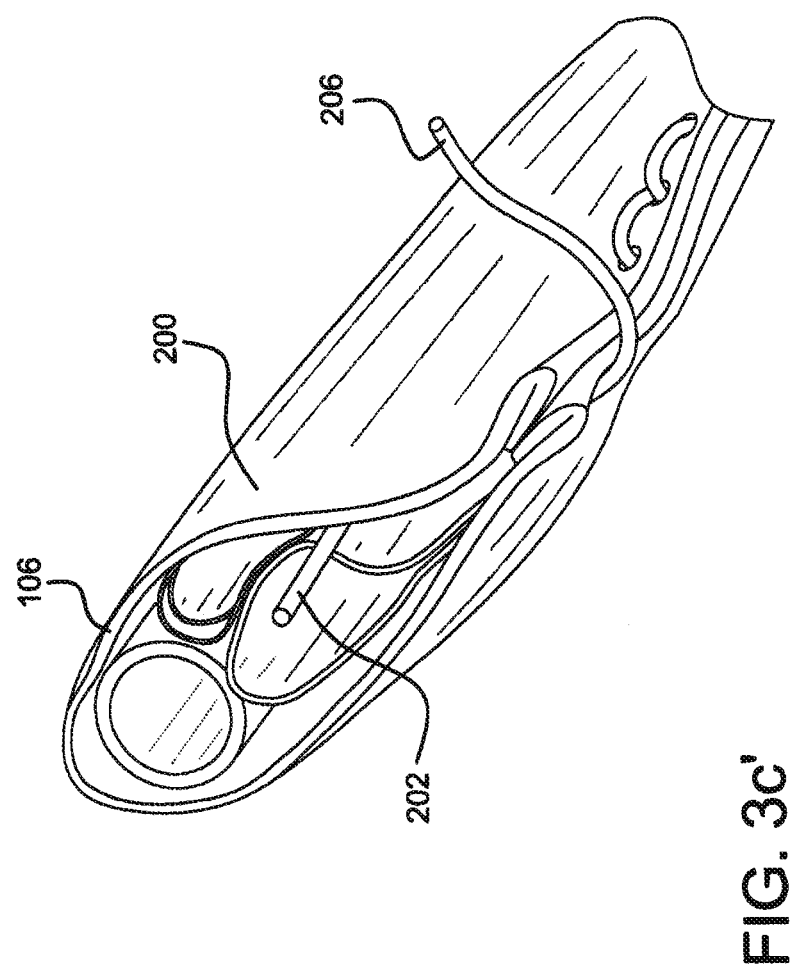

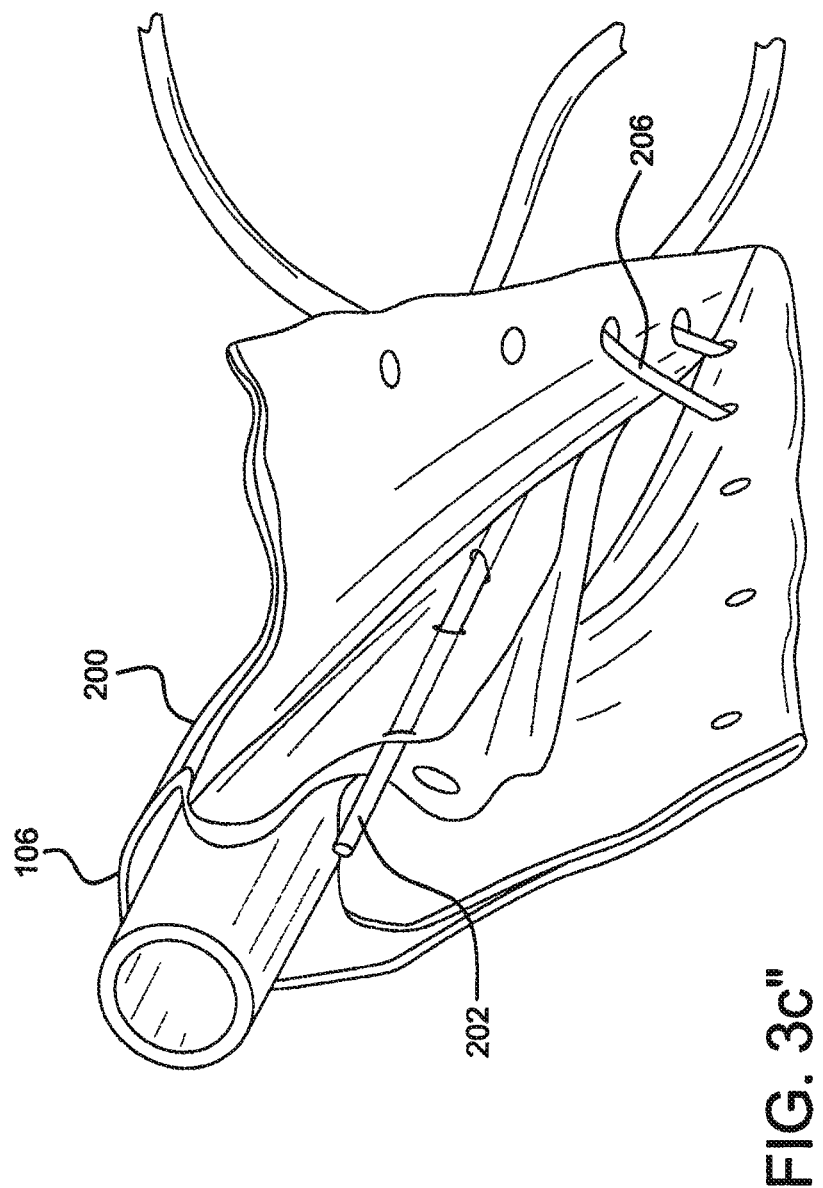
FIG. 3c"

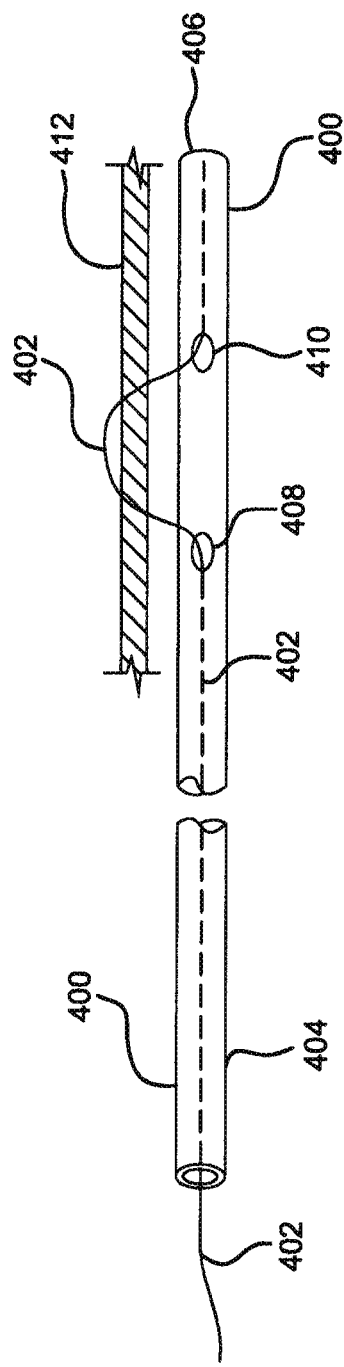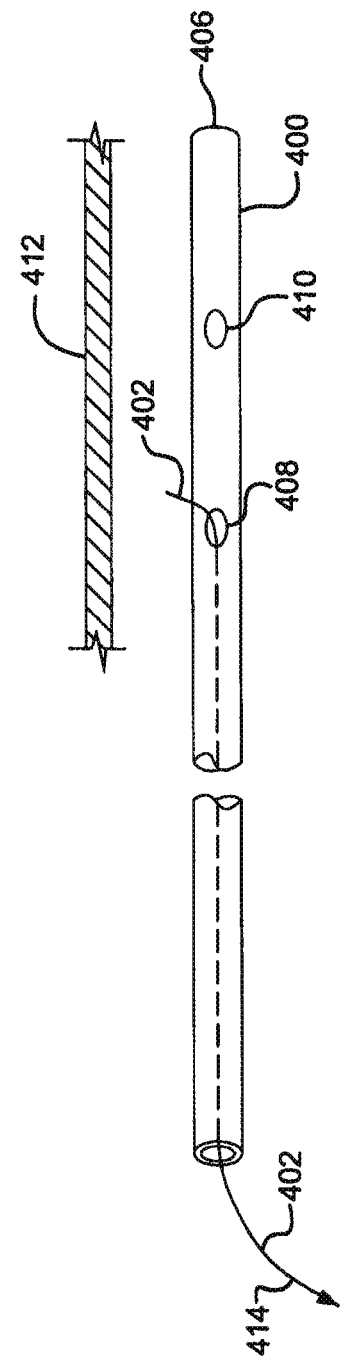

ns and releasably maintains the device 104 in a collapsed state or
APPOSITION FIBER FOR USE IN ENDOLUMINAL DEPLOYMENT OF EXPANDABLE DEVICES IN TORTUOUS ANATOMIES

CROSS REFERENCE TO RELATED APPLICATIONS

This application is a non-provisional of, and claims priority to, U.S. Provisional Patent Application No. 61/414,198, entitled "Apposition Fiber For Use In Endoluminal Deployment of Expandable Device in Tortuous Anatomies," filed Nov. 16, 2010, the content of which is hereby incorporated by reference in its entirety.

BACKGROUND

1. Field

The present disclosure relates to the transcatheter delivery and remote deployment of implantable medical devices and more particularly implantable intraluminal devices of either the self-expanding type or the balloon expandable type.

2. Discussion of the Related Art

Endoluminal therapies typically involve the insertion of a delivery catheter that transports an implantable prosthetic device into the vasculature through a small, often percutaneous, access site in a remote vessel. Once access to the vasculature is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Expandable endoprostheses are generally comprised of a stent component with or without a graft covering over the stent interstices. They are designed to spontaneously dilate (i.e., elastically recover) or to be balloon-expanded from their delivery diameter, through a range of intermediary diameters, up to a maximal, pre-determined functional diameter. The endoluminal delivery and deployment of expandable endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. A variety of ways of constraining and releasing an expandable device are known in the art.

It remains desirable to provide improved systems for endoluminal delivery of stents or stent grafts to vascular treatment sites. More particularly, it remains desirable to provide improved systems and methods for deploying an expandable device to a treatment site where surrounding anatomy at a treatment site is irregular or tortuous.

BRIEF DESCRIPTION OF THE DRAWINGS

In the following drawings:

FIGS. 4a through 4c are side views and a perspective view of a lock wire for releasably coupling the medical device to the catheter.

DETAILED DESCRIPTION OF THE ILLUSTRATED EMBODIMENTS

Figure 1:
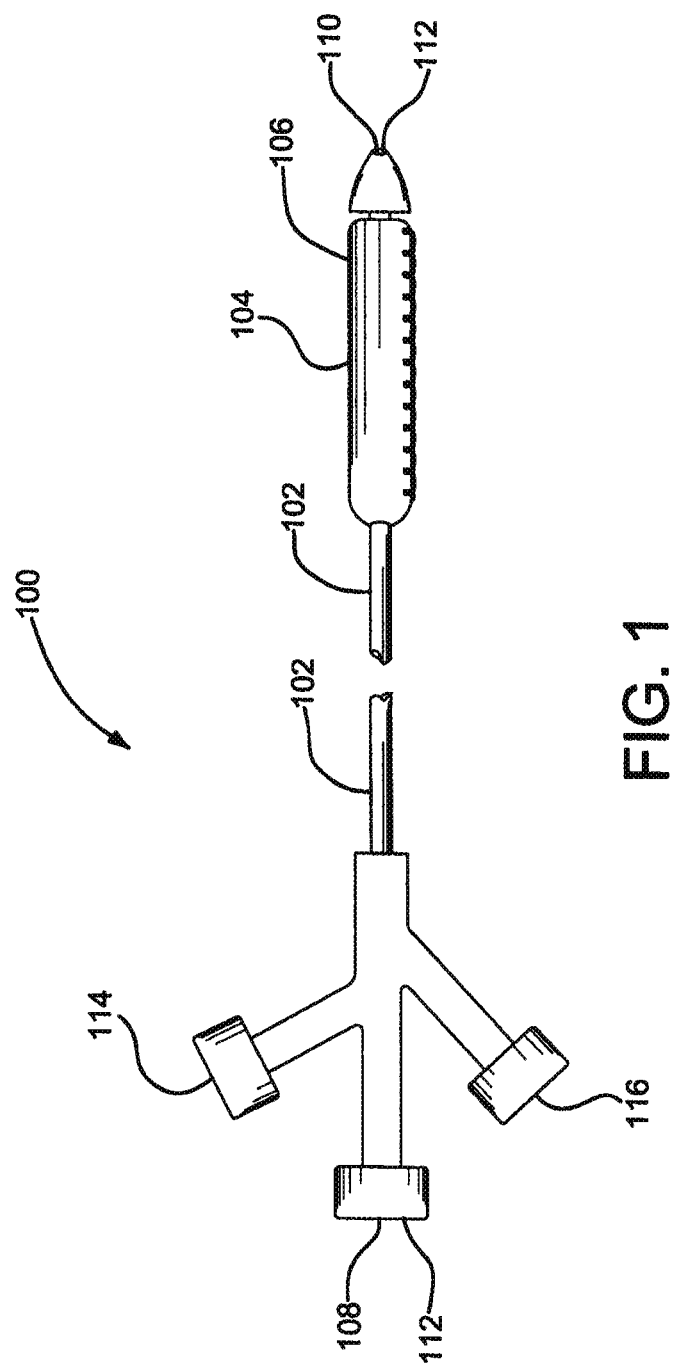
FIG. 1 is a side view of a catheter assembly having a compacted and constrained medical device near a distal end of the catheter.

Persons skilled in the art will readily appreciate that various aspects of the present disclosure can be realized by any number of methods and apparatuses configured to perform the intended functions. Stated differently, other methods and apparatuses can be incorporated herein to perform the intended functions. It should also be noted that the accompanying drawing figures referred to herein are not all drawn to scale, but can be exaggerated to illustrate various aspects of the present disclosure, and in that regard, the drawing figures should not be construed as limiting. Finally, although the present disclosure can be described in connection with various principles and beliefs, the present disclosure should not be bound by theory.

Throughout this specification and in the claims, the term "distal" can refer to a location that is, or a portion of an intraluminal device (such as a stent-graft) that when implanted is, further downstream with respect to blood flow than another portion of the device. Similarly, the term "distally" can refer to the direction of blood flow or further downstream in the direction of blood flow.

The term "proximal" can refer to a location that is, or a portion of an intraluminal device that when implanted is, further upstream with respect to blood flow. Similarly, the term "proximally" can refer to the direction opposite to the direction of blood flow or upstream from the direction of blood flow.

With further regard to the terms proximal and distal, and because the present disclosure is not limited to peripheral and/or central approaches, this disclosure should not be narrowly construed with respect to these terms. Rather, the devices and methods described herein can be altered and/or adjusted relative to the anatomy of a patient.

In various embodiments, for example as shown in FIG. 1, the catheter assembly, which is generally indicated at 100, includes a catheter 102, an expandable device 104 and a restraining member or flexible sleeve 106. The catheter 102 extends longitudinally and has opposite proximal 110 and distal 108 ends. The catheter 102 also includes a lumen 112 extending between the proximal 110 and distal 108 ends.

The expandable device 104 is disposed at or near the proximal end 110 of the catheter 102. The device 104 is expandable to engage surrounding tissue at the treatment site, such as inner surfaces of a vascular member. The device 104 can include a self-expanding nitinol frame that expands the device 104 upon deployment at the treatment site. The device 104 can also be balloon expandable.

In various embodiments, the flexible sleeve 106 extends around the device 104 and has a first outer peripheral dimension 208, at which the flexible sleeve 106 constrains and releasably maintains the device 104 in a collapsed state or small diameter delivery profile suitable for endoluminal delivery and advancement through typical vasculature to a treatment site. Fully opening the sleeve 106 allows the device 104 to fully expand toward an unconstrained or fully deployed outer peripheral dimension of the device 104, wherein the device 104 is fully expanded and not constrained by the flexible sleeve and/or vasculature. It should be appreciated that the device can be oversized relative to the intended vasculature to be treated to promote engagement between the device and the inner walls of the vasculature at the treatment site.

Figure 2A:
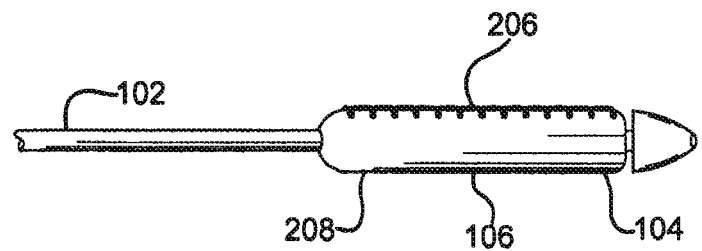
FIGS. 2a through 2c are partial side perspective views of an expandable medical device shown in various stages of deployment.

The flexible sleeve can have various configurations for constraining the sleeve. In various embodiments, the sleeve 106 includes generally opposite portions or edges each with a plurality of openings. The openings are arranged to form stitch lines that extend along the opposite portions of the sleeve 106. The sleeve 106 can extend around the device 104 and the opposite portions brought together to form a releasable seam 206, as shown in FIG. 2a. The releasable seam 206 can be held together by an elongated coupling member extending through or woven through the openings. Examples of coupling members include control tethers, wires, lines, and the like. The coupling member can extend through a catheter shaft 102 and be accessed through proximal connectors as indicated, for example, at 112, 114 or 116. Tensioning, actuation and displacement of the coupling member from the openings allows the sleeve 106 to open along the seam 206 and the device 104 to expand toward a larger diameter. Examples of restraining members and coupling members for releasably maintaining expandable devices in a collapsed state for endoluminal delivery can be found in U.S. Pat. No. 6,352,561 to Leopold et al, the content of which is incorporated herein by reference in its entirety.

Figure 2B:
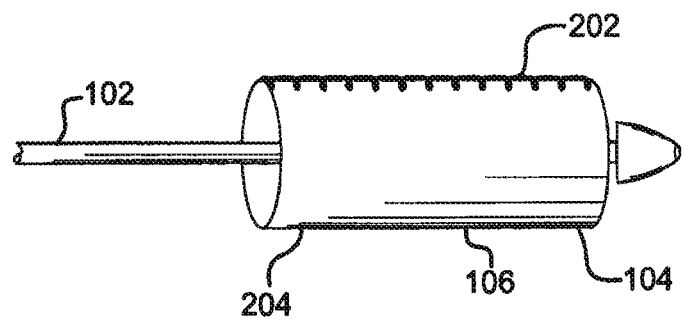

In various embodiments, the flexible sleeve 106 can be configured to maintain the device 104 in an intermediate state, as illustrated in FIG. 2b, in which the sleeve 106 is maintained at a second outer peripheral dimension that is larger than the first outer peripheral dimension of the sleeve 106, yet smaller than the fully deployed outer peripheral dimension of the device 104. Thus, when the device 104 is positioned generally at or near the treatment site, the flexible sleeve 106 can be actuated to allow the sleeve 106 to expand or be pushed outwardly toward the intermediate state by a generally radially outward force applied by expansion of the device 104 by, for example, a balloon and/or by a stent or wire frame portion of the device. Maintaining the device in the intermediate state allows the clinician to adjust the axial and/or rotational position of the device with respect to the vasculature prior to full release and expansion of the device toward the fully deployed outer peripheral dimension and engagement with surrounding vasculature tissue.

In various embodiments, the sleeve is maintained in this intermediate state or second outer peripheral dimension 204 by a second releasable seam 202 held together by a portion of the same coupling member used to secure the first releasable seam or, alternatively, by a separate coupling member separate from the first releasable seam. Thus, in various embodiments, a single flexible sleeve is formed having a multi-stage deployment. In a dual stage configuration, for example, the sleeve can have a first outer peripheral dimension, indicated at 208 in FIG. 2a, releasably maintained by a first releasable seam 206 and a second outer peripheral dimension, indicated at 204 in FIG. 2b, releasably maintained by a second releasable seam 202. In various other embodiments, the sleeve can be formed with more than two states or stages and associated multiple outer peripheral dimensions can be utilized leading toward the final fully deployed outer peripheral dimension by incorporating additional releasable seam arrangements.

Figure 3A:
FIGS. 3a through 3c, 3c' and 3c" are side views and perspective views depicting a method of making a flexible constraining sleeve with two releasable seams.
Figure 3B:
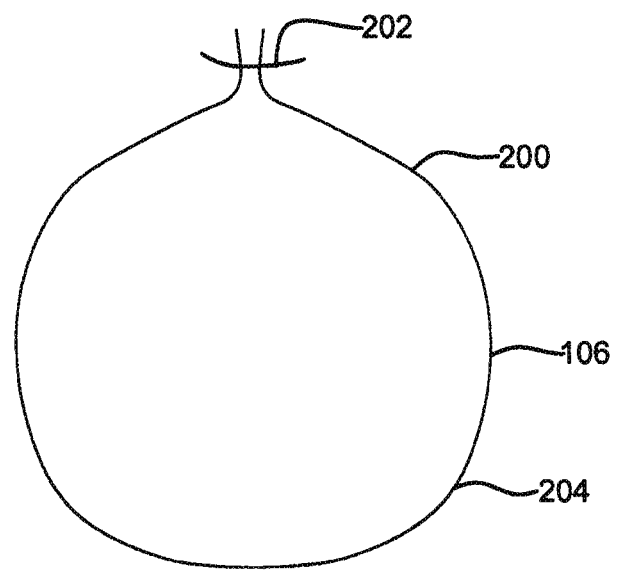
Figure 3C:
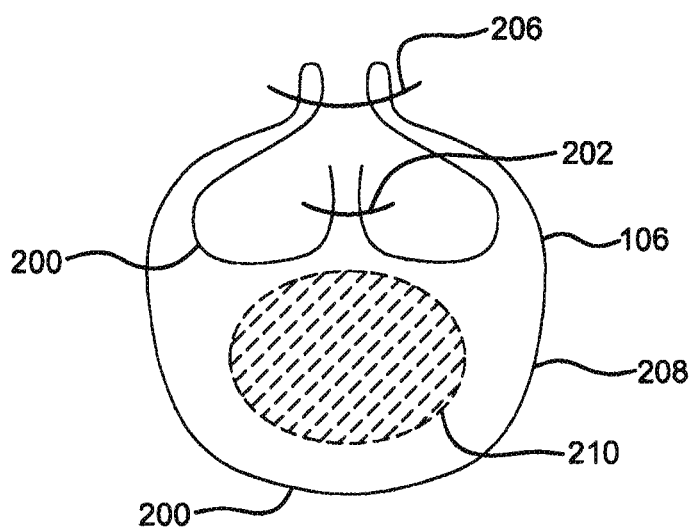

A method of forming a restraining member in accordance with the present disclosure is generally illustrated by the sequence of FIGS. 3a through 3c, 3c', 3c" in which a restraining member have a multi-stage deployment is formed by interconnecting portions of a flexible sheet together to form a releasable seam to define a lumen with a first outer peripheral dimension and interconnecting other portions of the flexible sheet together to form another releasable seam to reduce the size of the lumen to a second outer peripheral dimension. Shown in FIG. 3a is an edge view of a flexible sheet material 200 that will be subsequently formed into a restraining member.

The sheet 200 is folded over onto itself to form a lumen, as shown in FIG. 3b. Portions or edges of the folded sheet 200 are then stitched with a coupling member to form a releasable seam 202. The resulting lumen limits expansion of the device to the intermediate state, as discussed above.

Other portions of the flexible sheet are then folded and interconnected to form an additional releasable seam 206, as shown in FIGS. 3, 3c', 3c", to further reduce the size of the lumen to an outer peripheral dimension suitable for endoluminal delivery of the device. The cross sectional area 210 roughly illustrates the area in which the device will be constrained.

The seams 202, 206, as shown in FIG. 3C, are generally radially aligned or positioned substantially along the same side of the area 210. In various other embodiments, however, the seams can be offset rotationally about the area 210. The seams, for example, can be disposed on opposite sides of the area 210 relative to each other.

To reiterate the delivery sequence, the device (FIG. 1, 104) is initially constrained to a small diameter delivery state as shown in FIG. 2a. The flexible sleeve 106, while in this small diameter state, has a small or first outer peripheral dimension 208 suitable for endoluminal delivery of the device to a treatment site. When the releasable first seam 206 is actuated, the sleeve 106 will expand to a larger diameter state or second outer peripheral dimension 204, as shown in FIG. 2b, due to a generally radially outward force applied by the expansion of the device 104, either by balloon and/or by a stent or wire frame portion of the device. To complete delivery or full deployment of the device at the treatment site, the releasable second seam 202 is actuated which splits open the sleeve 106 to allow the device to expand toward the fully deployed outer peripheral dimension and engage surrounding tissue at the treatment site.

In various embodiments, a flexible sleeve used for a constraint can comprise materials similar to those used to form a graft. In various embodiments, the precursor flexible sheet (FIG. 2a, 200) can be formed from a flattened, thin wall tube so that the resulting lumen is double-walled. In various embodiments, a precursor flexible sheet or flattened thin wall tube can incorporate "rip-stops" in the form of longitudinal high strength fibers attached or embedded into the sheet or tube wall.

To allow manipulation and repositioning of the partially expanded device via a catheter, the device, in various embodiments, is releasably coupled to the catheter. In various embodiments, a partially or fully expanded stent or stent graft may be releasably coupled to a catheter by, for example, removable tie-lines, clips and the like.

Figure 4C:
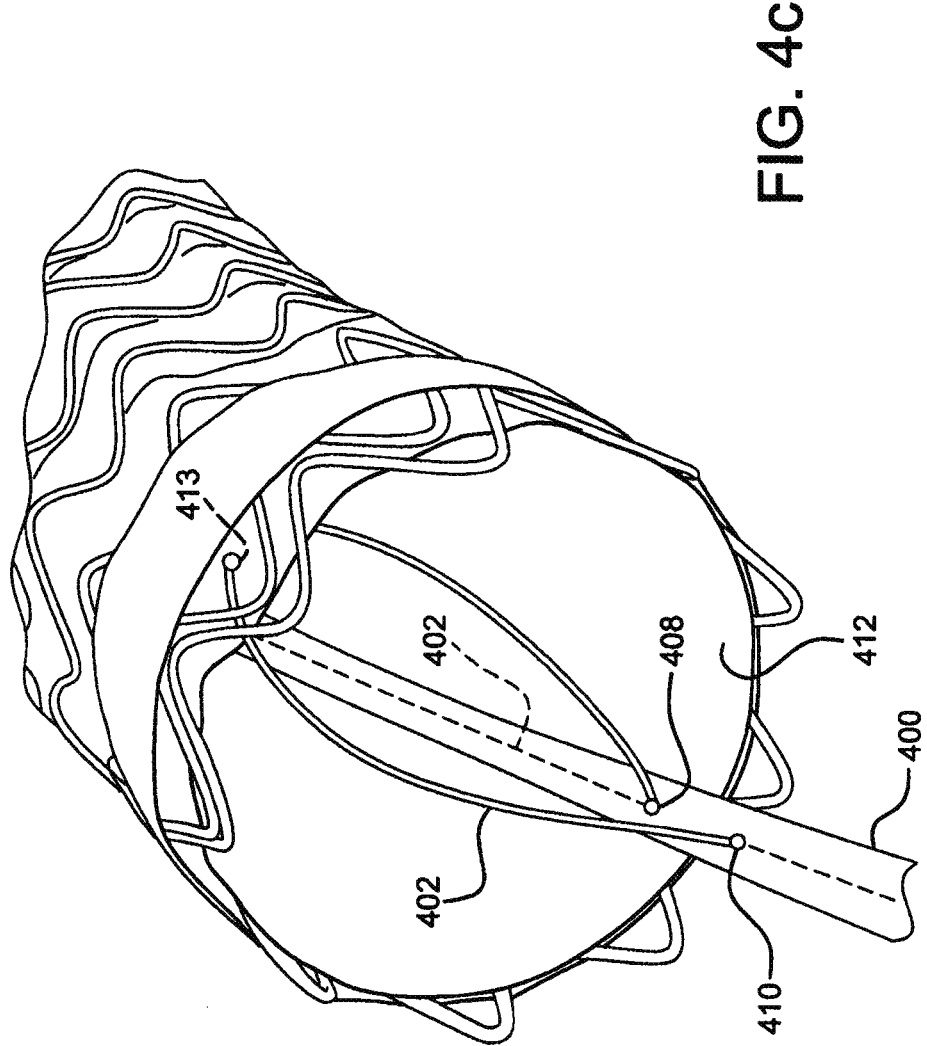

In other embodiments, as shown in FIGS. 4a and 4c, a catheter shaft 400 having generally opposite distal 404 and proximal ends 406 is positioned adjacent a stent graft wall 412, either internally or externally with respect to the stent graft. To releasably couple the catheter shaft 400 to the stent graft wall 412, an elongated member 402, such as a wire, can extend through a distal end 404 of the catheter shaft 400. The elongated member 402 can further extend through the catheter lumen and extend outwardly through a distal side wall opening 408. The elongated member can form a loop, penetrating the graft wall 412 through at least one aperture 413 in the graft wall 412 and returning into the catheter lumen through a proximal side wall opening 410. The elongated member 402 is, by this arrangement, releasably coupled to the graft wall, allowing manipulation and repositioning of the graft as required. Alternatively, the elongated member can extend through an apice of a wire frame or at least extend around a portion of the wire frame to releasably couple the catheter shaft to the stent graft wall.

When the graft is positioned at a desired location along the treatment site, the catheter 400 can be disengaged from the graft wall 412 to allow removal of the catheter from the treatment site and allow the stent graft to remain in place at the treatment site. More specifically, as shown in FIG. 4b, the catheter can be released from the graft wall by retracting the elongated member 402 in a distal direction as depicted by direction arrow 414. The elongated member can exit both catheter side wall holes 408, 410 and be fully withdrawn from the catheter lumen.

An elongated member 402, as shown in FIG. 4b, can be threaded through a graft wall, through a stent frame or through a graft/stent coupling element such as a hook. In various embodiments, elongated members can also be attached to a graft through a "cork-screw" configuration. Such a cork-screw can be twisted to engage and penetrate a graft wall (or lock to a stent frame) and be un-twisted to release the elongated member from the graft/stent.

Elongated members or lock wires, in various embodiments, can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol. In other various embodiments, elongated members or lock wires can also be formed from high strength polymer fibers such as ultra high molecular weight polyethylene fibers (e.g., Spectra®, Dyneema Purity®, etc.) or aramid fibers (e.g., Technora®, etc.).

Figure 2C:
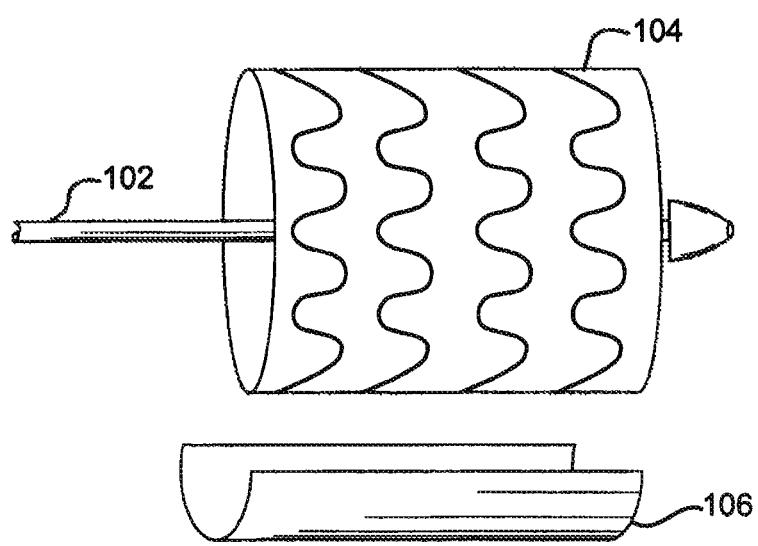

When the graft is positioned at a desired location along the treatment site, the flexible sleeve 106 can be further actuated to allow the sleeve 106 to "split open" and fully release the device 104, as illustrated in FIG. 2c. The device 104 can then expand toward the fully deployed outer peripheral dimension and engage the vascular wall. Referring back to FIG. 4b, the catheter can be released from the graft wall of the now-deployed device 104 by retracting the elongated member 402 in a distal direction as depicted by direction arrow 414. The elongated member can exit both catheter side wall holes 408, 410 and be fully withdrawn from the catheter lumen.

Stents can have various configurations as known in the art and can be fabricated, for example, from cut tubes, wound wires (or ribbons) or flat patterned sheets rolled into a tubular form. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

Potential materials for a graft member include, for example, expanded polytetrafluoroethylene (ePTFE), polyester, polyurethane, fluoropolymers, such as perfouorelastomers and the like, polytetrafluoroethylene, silicones, urethanes, ultra high molecular weight polyethylene, aramid fibers, and combinations thereof. One preferred embodiment for a graft material is ePTFE. Other embodiments for a graft member material can include high strength polymer fibers such as ultra high molecular weight polyethylene fibers (e.g., Spectra®, Dyneema Purity®, etc.) or aramid fibers (e.g., Technora®, etc.). The graft member can include a bioactive agent. In one embodiment, an ePTFE graft includes a carbon component along a blood contacting surface thereof.

Typical materials used to construct catheters can comprise commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX) and metals such as stainless steel and nickel/titanium alloys.

Figure 10:
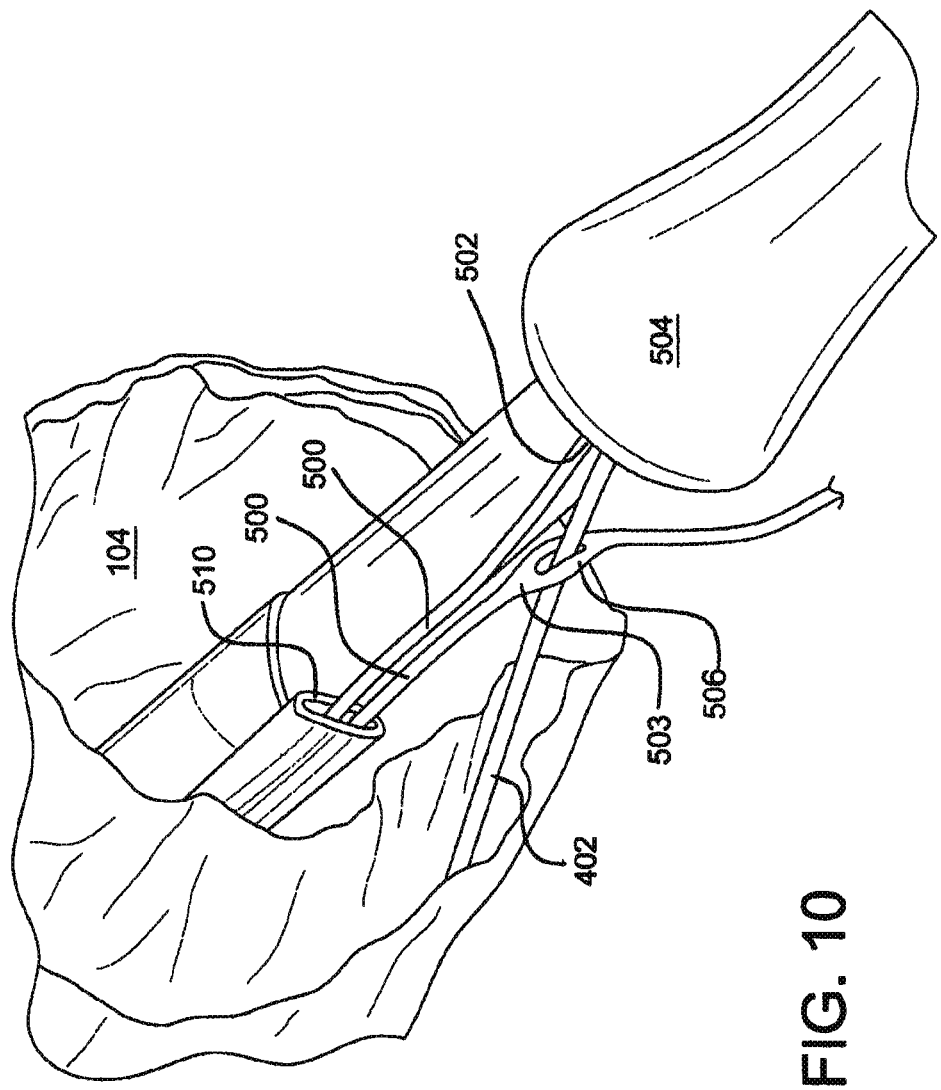

In various embodiments, a line or fiber can be used to facilitate deployment of an expandable device at tortuous treatment sites, such as the aortic arch, where an end of the expandable device might otherwise fail to conform, engage, and form a seal with the surrounding tissue due to straightening out or rotation of the end of the expandable device. In various embodiments, for example as shown in FIGS. 5-10, a fiber 500 extends between one end 502 fixedly secured to a proximal catheter olive 504 and an opposite end 503 having an eyelet 506 (FIG. 10). More specifically, as part of the catheter assembly, the fiber 500 extends from one end 502 at the catheter olive 504, through a lumen 510 in the catheter 102, penetrates the side wall 104a of the device 104 near or at the proximal end of the device 104 (FIG. 9), and returns through the lumen 510 toward the catheter olive 504. The elongated member 402 (FIG. 4) extends through the eyelet 506 and retains the end 502 of the fiber 500 proximal to the catheter olive 504. In various embodiments, the fiber 500 can extend and loop around wire frame apices 104b as well as or instead of through the side wall 104a, as earlier described.

Figure 5:
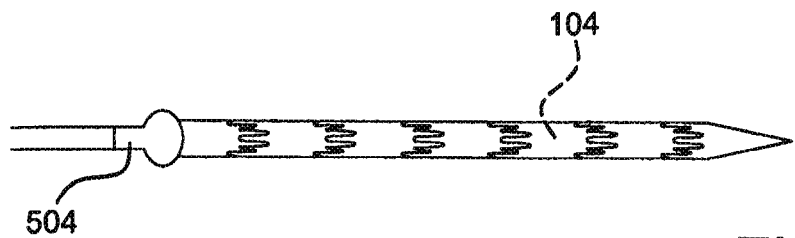
FIGS. 5-10 illustrate another embodiment including a fiber holds an inner curve of the device and thereby facilitates deployment of the device at tortuous treatment sites.
Figure 6:
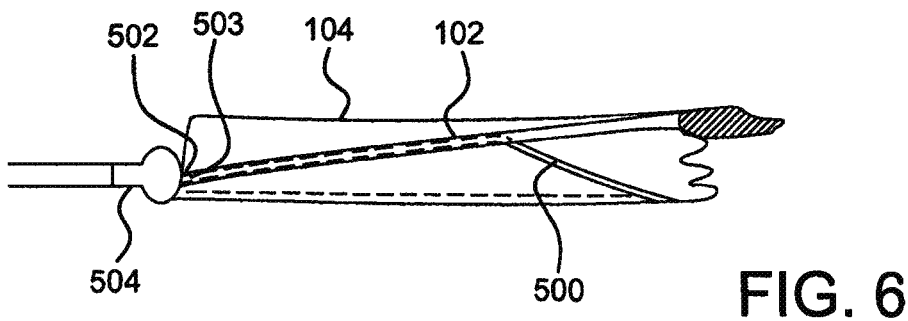
Figure 7:
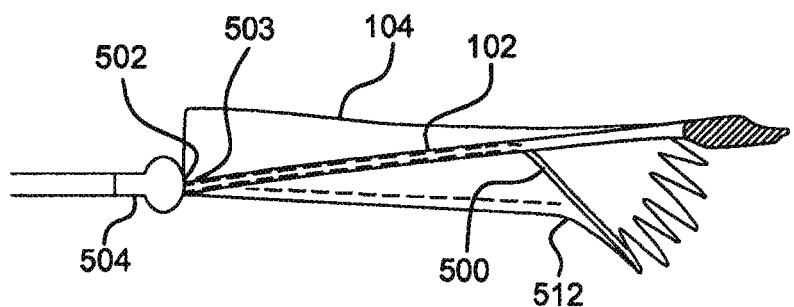
Figure 8:
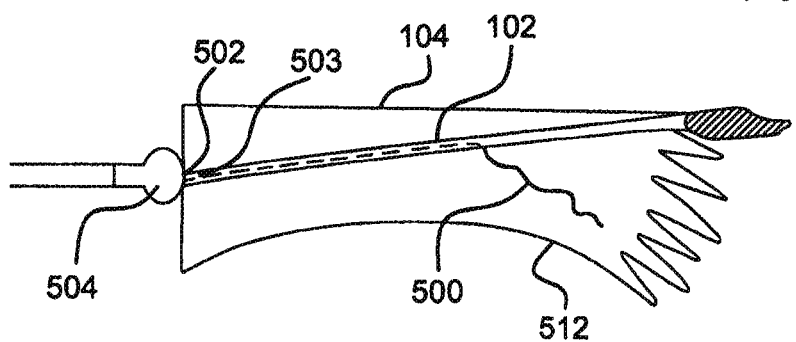
Figure 9:
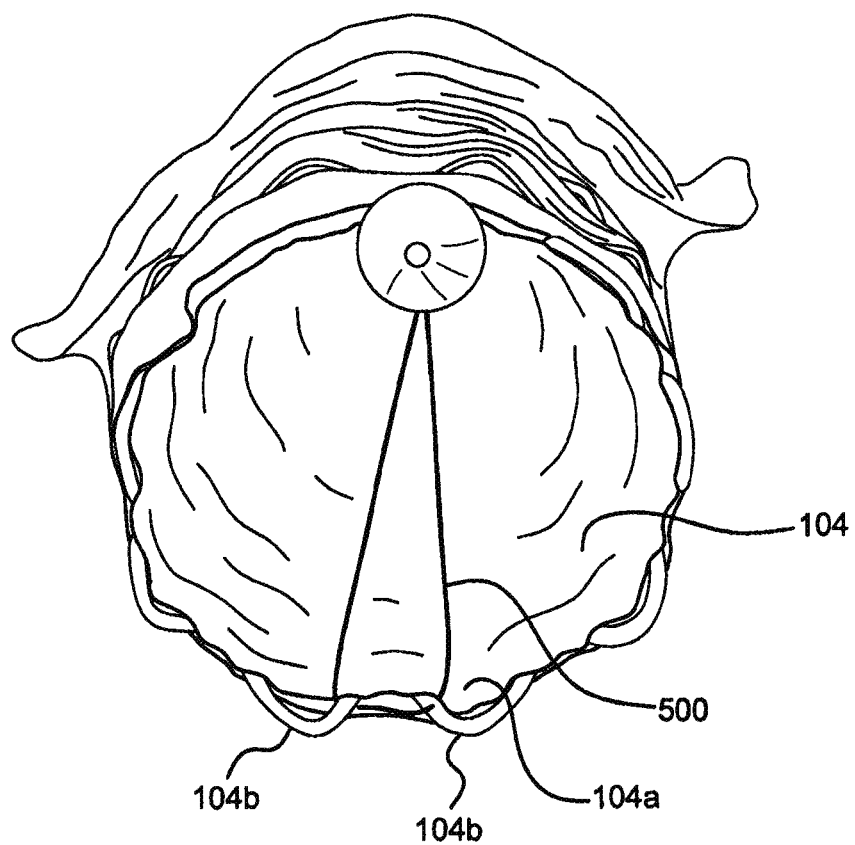

FIGS. 5-8, in order, generally illustrate a deployment sequence of the device utilizing the fiber 500 to hold an inner curve of the device 104 as it is deployed along a curved or tortuous anatomy, such as the aortic arch. In FIG. 5, the device 104 is constrained in a flexible constraining sleeve and deployed endoluminally toward a tortuous treatment site. In FIG. 6, the device 104 is partially deployed near the treatment site to a second intermediate state (illustratively described above and shown in FIG. 2b). In this state, the device 104 can be further manipulated to a final desired deployment location and position. In FIG. 7, the device 104 is allowed to expand fully toward the surrounding tissue at the treatment site. The fiber 500 maintains an inner curve (generally indicated at 512) which generally conforms with the tortuous anatomy at the treatment site. Maintaining the inner curve 512 allows the device 104 to fully engage the surrounding tissue and form a seal therewith. In FIG. 8, the fiber 500 is disengaged as the device is fully deployed by pulling the elongated member 402 (as described above). The elongated member 402 is pulled from the eyelet 506, which allows the fiber 500 to be retracted from the treatment site with the catheter after successful deployment of the device at the treatment site.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A catheter assembly comprising:
a catheter having opposite proximal and distal ends, the catheter having a lumen extending between the proximal and distal ends of the catheter;
an expandable device disposed at the distal end of the catheter and expandable toward a fully deployed outer dimension;
a fiber extending from the catheter and releasably coupled to a side wall of the expandable device near or at an end of the expandable device to maintain an inner curvature of the expandable device as the expandable device is deployed; and
an elongated member that extends through the catheter and through the side wall of the expandable device to releasably couple the device to the catheter, wherein the elongated member extends through an eyelet at an end of the fiber releasably coupling the fiber to the expandable device.

2. The catheter assembly as set forth in claim 1, wherein a fixed end of the fiber opposite the eyelet is fixedly secured to the catheter.

3. The catheter assembly as set forth in claim 2, wherein the fiber extends from the fixed end through a lumen in the catheter, penetrates the side wall of the expandable device, and returns through the lumen to a point proximal the fixed end.

4. The catheter assembly as set forth in claim 3, wherein the elongated member extends through the eyelet at the point proximal the fixed end.

5. The catheter assembly as set forth in claim 1, wherein the side wall of the expandable device includes a wire frame, the fiber being releasably coupled about a portion of the wire frame.

6. A catheter assembly comprising:
a catheter having opposite proximal and distal ends, the catheter having a lumen extending between the proximal and distal ends of the catheter;
an expandable device releasably coupled to the catheter and expandable toward a fully deployed outer peripheral dimension;
a flexible sleeve extending around the device, the sleeve having a releasable first seam that maintains the sleeve at a first outer peripheral dimension suitable for endoluminal delivery and deployment of the device to a treatment site, and a releasable second seam that limits expansion of the sleeve to a second outer peripheral dimension larger than the first outer peripheral dimension and smaller than the fully deployed outer peripheral dimension after release of the releasable first seam; and
a fiber extending from the catheter and releasably coupled to a side wall of the expandable device near or at an end of the expandable device to maintain an inner curvature of the expandable device as the expandable device is deployed.

7. The catheter assembly as set forth in claim 6 including an elongated member that extends through the catheter and through the side wall of the expandable device to releasably couple the device to the catheter.

8. The catheter assembly as set forth in claim 7, wherein the elongated member extends through an eyelet at an end of the fiber releasably coupling the fiber to the expandable device.

9. The catheter assembly as set forth in claim 8, wherein a fixed end of the fiber opposite the eyelet is fixedly secured to the catheter.

10. The catheter assembly as set forth in claim 9, wherein the fiber extends from the fixed end through a lumen in the catheter, penetrates the side wall of the expandable device, and returns through the lumen to a point proximal the fixed end.

11. The catheter assembly as set forth in claim 10, wherein the elongated member extends through the eyelet at the point proximal the fixed end.

12. The catheter assembly as set forth in claim 6, wherein the side wall of the expandable device includes a wire frame, the fiber being releasably coupled about a portion of the wire frame.

* * * * *